United States Patent [19]

Felder et al.

[11] 4,352,788

[45] Oct. 5, 1982

[54] DERIVATIVES OF 2,4,6-TRIIODO-ISOPHTHALIC ACID, PROCESSES FOR THEIR SYNTHESIS AND X-RAY CONTRASTING MATERIALS CONTAINING THESE

[75] Inventors: Ernst Felder, Riva S. Vitale, Switzerland; Davide Pitre, Milan, Italy

[73] Assignee: Bracco Industria Chimica S.p.A., Milan, Italy

[21] Appl. No.: 173,698

[22] Filed: Jul. 30, 1980

[30] Foreign Application Priority Data

Aug. 9, 1979 [IT]  Italy ............................... 25026 A/79

[51] Int. Cl.³ ............................................. A61K 49/04
[52] U.S. Cl. ......................................... 424/5; 564/153
[58] Field of Search ............................. 424/5; 564/153

[56] References Cited

U.S. PATENT DOCUMENTS

| | | | |
|---|---|---|---|
| 3,632,738 | 1/1972 | Ingelman | 424/5 |
| 3,678,152 | 7/1972 | Bjork et al. | 424/5 |
| 4,239,747 | 12/1980 | Pfeiffer et al. | 424/5 |
| 4,250,113 | 2/1981 | Nordal et al. | 564/153 |

FOREIGN PATENT DOCUMENTS 2457789  6/1975  Fed. Rep. of Germany .......... 424/5

*Primary Examiner*—Delbert K. Phillips
*Attorney, Agent, or Firm*—Toren, McGeady & Stanger

[57] ABSTRACT

Compounds for use in non-ionic X-ray contrasting materials having the formula

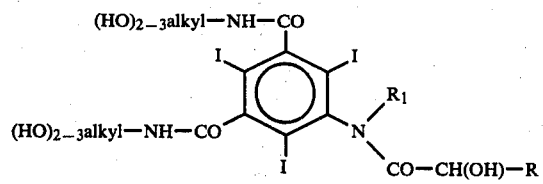

in which
(HO)$_{2-3}$alkyl is 1,3-dihydroxyisopropyl, 2,3-dihydroxypropyl or 1,3-dihydroxy-2-hydroxymethylisopropyl,
R is hydrogen or methyl, and
R$_1$ is an alkyl residue with 1 to 5 carbon atoms.

These compounds possess high water-solubility as well as excellent stability against hydrolysis. Methods for preparation and use of the compounds are also disclosed.

6 Claims, No Drawings

DERIVATIVES OF 2,4,6-TRIIODO-ISOPHTHALIC ACID, PROCESSES FOR THEIR SYNTHESIS AND X-RAY CONTRASTING MATERIALS CONTAINING THESE

BACKGROUND OF THE INVENTION

1. Field of the Invention

The present invention relates to novel, readily water-soluble 5-(N-alkyl-α-hydroxyacyl-amino)-2,4,6-triiodo-isophthalic-acid-bis-(hydroxyalkyl-amides) suitable for use as X-ray contrast agents.

2. Description of the Prior Art

5-Acylamino-2,4,6-triiodo-isophthalic acid diamides and their use in X-ray contrasting materials are disclosed in Swiss Pat. No. 544,551. They contain only simple, unsubstituted aliphatic acyl groups, usually acetyl groups. Some representatives of this group, which contain carbohydrate residues, are readily water-soluble, for example, the 3-acetylamino-5-N-methyl-acetylamino-2,4,6-triiodo-benzoyl-glucosamine, which has become known under the non-proprietary name of METRIZAMIDE. In this connection, see also compound No. 11 of U.S. Pat. No. 3,701,711, British Pat. No. 1,321,591, Swiss Pat. No. 554,551, Austrian Pat. No. 318,134 and German Offenlegungsschrift No. 2,031,724, as well as publications by T. Almen, S. Salvesen, K. Golman: Acta Radiologia Suppl. 335 (1973), 1–13, 233–75, 312–38.

One of the disadvantages with this compound is that it is difficult to obtain. This is because it is present in the form of a mixture of isomers and it is practically impossible to isolate the individual isomers, and primarily because it has relatively little stability in aqueous solutions. This makes the handling of the material difficult and significantly limits its usefulness.

The 1-5-α-hydroxypropionylamino-2,4,6-triiodophthalic-acid-bis-(1,3-dihydroxyisopropylamide) represents an advance over this compound and has become known under the non-proprietary name of IOPAMIDOL. In this connection, see German Pat. No. 2,547,789, British Pat. No. 1,472,050, U.S. Pat. No. 4,001,323 and the article by Felder et al., IL FARMACO, Ed. Sc. 32, 835–844 (1977). It is distinguished by an essentially simpler structure, by higher stability, by a lower viscosity of its concentrated aqueous solutions and by being more easily isolated. The toxicity of this compound is very low.

Recently, two additional derivatives of 5-acylamino-2,4,6-triiodo-isophthalic acid, namely, 5-(N-2-hydroxyethylacetyl-amino)-2,4,6-triiodoisophthalic-acid-bis-(2,3-dihydroxypropylamide) and 5-(N-2,3-dihydroxypropyl-acetylamino)-2,4,6-triiodoisophthalic-acid-bis-(2,3-dihydroxypropylamide), which have similar properties, were disclosed in Belgian patent 855,850. They are derived from the slightly water-soluble 5-acetylamino-2,4,6-triiodoisophthalic-acid-bis-(2,3-dihydroxypropylamide), the water solubility of which is 1% (w/v) at 20°–40° C. It is therefore not surprising that some pertinent isomers are insoluble in water and therefore, practically unusable (see, for example, Belgian Pat. No. 855,850, pages 21–22).

The developments in recent years have clearly shown that it is extremely difficult and only infrequently possible to find compounds which have the properties required for use in nonionic X-ray contrasting materials. These properties are a true water solubility sufficient for producing stable, that is, not supersaturated, concentrated solutions, maximum general and neurotropic tolerance, minimum osmolality, slight viscosity, maximum stability towards hydrolytic effects and a sufficiently simple structure to make the synthesis economical as well as to simplify the isolation and purification.

SUMMARY OF THE INVENTION

We have discovered a select group of novel compounds which possess these properties and a simple method for preparing these compounds. More particularly, the compounds of the present invention have the formula

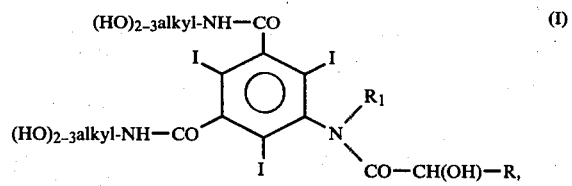

in which $(HO)_{2-3}$alkyl represents 1,3-dihydroxyisopropyl, 2,3-dihydroxypropyl or 1,3-dihydroxy-2-hydroxymethylisopropyl, R represents hydrogen or methyl; and $R_1$ represents an alkyl residue with 1 to 5 carbon atoms, of which methyl, ethyl and propyl are preferred.

These compounds simultaneously possess high water solubility which reaches absolute peak values in some instances, optimum tolerance and relatively slight osmolalities, as well as high stability towards hydrolytic influences, and the good stability of the starting materials, which are not alkylated at the aromatic nitrogen atom and on which they are based. This enhanced stability towards hydrolytic influences is important for preventing even the trace formation of free aromatic amines to avoid any possible cytotoxic effect of these amines in conjunction with X-rays. In this connection, see A. Norman et al., Radiology 129, 199–203 (October 1978).

The compounds of the present invention are prepared by alkylation of 5-α-hydroxyacylamino-2,4,6-triiodo-isophthalic-acid-bis-(dihydroxy-propylamide) of the general formula (III)

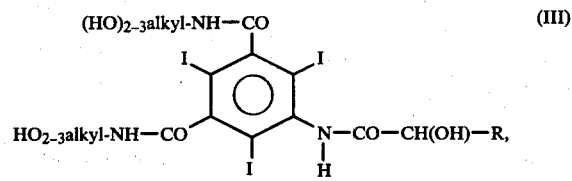

at the aromatic nitrogen in an alkaline medium by reaction with alkylating agents of the general formula (IV)

in which

R and $R_1$ in formulas (III) and (IV) have the meaning defined hereinbefore, and X represents a halogen atom, iodine, bromine or chlorine or a sulfate or sulfonate radical ($-OSO_2-OR_1$ or $-OSO_2-$alkyl or $-OSO_2-$aryl), or reacting a reactive functional derivative of a 5-(N-alkyl-α-hydroxyacyl-amino)-2,4,6-triiodo-isophthalic acid of the general formula (V)

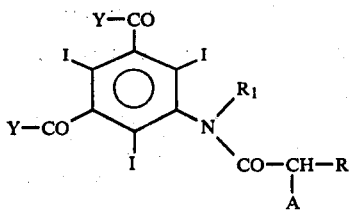

in which

R and R₁ have the above-defined meaning,

A represents a low molecular weight acyloxy residue with about 1 to 5 carbon atoms or a halogen atom and Y—CO— reactive acid halide or acid anhydride radicals whose hydroxy function may be masked by acetalization or ketalization, the masking function A and any acetal or ketal functions present in the 5-(N-alkyl-α-hydroxyacyl-amino)-2,4,6-triiodo-isophthalic-acid-bis-(hydroxy-alkylamide) derivative then being split off into hydroxy functions.

DESCRIPTION OF THE PREFERRED EMBODIMENTS

The viscosity of the aqueous solutions of these compounds is very dependent on their specific structure. It may vary greatly and may therefore be matched optimally to the most widely differing requirements of the respective uses.

It is particularly surprising and, at the same time, valuable that, as a result of the attachment even of low molecular weight, unsubstituted, that is, hydrophobic alkyl residues to the aromatic nitrogen atom in the 5-position of the basic compound, for example, 1-5-α-hydroxypropionylamino-2,4,6-triiodo-isophthalic-acid-bis-(1,3-dihydroxyisopropylamide)=IOPAMIDOL or 5-hydroxyacetylamino-2,4,6-triiodo-isophthalic-acid-bis-(2,3-dihydroxypropylamide), the water solubility is not only maintained but even considerably enhanced, particularly in the case of N-methyl compounds.

In addition, the stability towards hydrolytic effects is also increased. The water solubility of IOPAMIDOL at 20° C. corresponds to 440 mg of iodine per ml (that is, 89.7% w/v) and that of the hydrate to 307 mg of iodine per ml (that is 62.7% w/v). The 5-N-alkyl derivatives on the other hand, which fall within the scope of the present invention, have water solubilities of 100% (w/v). In addition, their hydrolysis stability is greater than that of the corresponding compounds which have not been alkylated.

Because of their outstanding properties, especially their good water solubility, their nonionic character, their high stability, their very good tolerance and comparatively relatively simple structure, the inventive, novel X-ray contrasting materials have a very broad application spectrum. They can be synthesized quite economically and can therefore be used for purposes for which the permissible costs of the contrasting material are limited.

The focal point of their use is the visualization of vessels, that is, angiography, such as, for example, ateriography, the visualization of the heart (cardiography) and of the coronary vessels (coronar graphy), the abdominal, the selective abdominal and the thoracic aortography, renal and cerebral angiography, phlebography as well as urography and the enhancement of contrast in computer tomography. In the case of the last-mentioned application, very large quantities of contrasting materials are required, for example, 250 ml of contrasting material solution with 300 mg of iodine per ml, containing a total of 75 g of iodine. Understandably, in the case of such large dosages for purely diagnostic purposes, the requirements in regard to tolerance and safety are exceptionally high. Further areas of application are, for example, bronchography, the visualization of body cavities and of fluid cavities as well as lymphangiography.

The 5-(N-methyl-α-hydroxyacyl-amino)-2,4,6-triiodo-isophthalic-acid-bis-(hydroxyalkylamides) of the general formula (II)

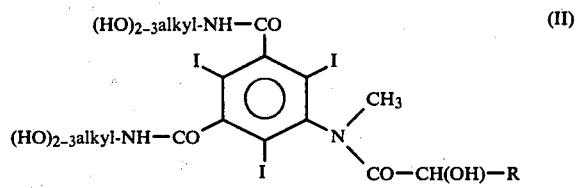

in which $(OH)_{2-3}$alkyl represents 1,3-dihydroxyisopropyl, 2,3-dihydroxypropyl or 1,3-dihydroxy-2-hydroxymethylisopropyl and R represents hydrogen or methyl, are radio-opaque components, which are distinguished in general by their particularly high water-solubility and their low viscosity. They are exceptionally suitable for the aforementioned uses.

In preparation of the components of the present invention, a suitable 5-α-hydroxyacylamino-2,4,6-triiodo-isophthalic-acid-bis-(hydroxyalkylamide) is reacted in the presence of bases with an alkyl halide, alkyl sulfate or an appropriate alkyl sulfonate, for example, an alkyl ester of methanesulfonic acid, benzenesulfonic acid or toluenesulfonic acid.

Typical concrete examples of alkylating agents of formula $R_1$-X are:

methyl bromide, methyl iodide, methyl chloride, dimethyl sulfate, methyl methanesulfonate, methyl benzenesulfonate, methyl toluenesulfonate, ethyl bromide, ethyl iodide, diethyl sulfate, ethyl methanesulfonate, ethyl benzenesulfonate, ethyl toluenesulfonate, propyl bromide, propyl iodide, propyl sulfate, propyl methanesulfonate, propyl benzenesulfonate, propyl toluenesulfonate, butyl bromide, butyl iodide, dibutyl sulfate, butyl methanesulfonate, butyl benzenesulfonate, butyl toluenesulfonate, amyl iodide, amyl bromide, amyl methanesulfonate, amyl benzenesulfonate, amyl toluenesulfonate.

The strong acid (HX), which is released during the alkylation, is neutralized by the base which is present. The following may be used as bases: strong alkalies, such as, for example, alkali alcoholates (NaOMe, NaOEt, KOMe, KOEt, LiOMe, LiOEt), alkali hydroxides (NaOH, KOH, LiOH), alkali carbonates ($Na_2CO_3$, $K_2CO_3$), and quaternary ammonium hydroxides (tetramethylammonium hydroxide).

The reaction is usually carried out in a polar solvent, such as, for example, water, lower alcohols, (MeOH, EtOH, ethylene glycol, propylene glycol, glycerin), lower glycol ethers (methoxyethanol, ethoxyethanol, butoxyethanol), ketones, (acetone, methyl ethyl ketone, methyl isopropyl ketone, methyl isobutyl ketone) or in a decidedly aprotic solvent, such as, for example, hexametanol (MPT), dimethyl formamide (DMF), dimethylacetamide (DMAC), and dimethylsulfoxide (DMSO), or in solvent mixtures. The reaction is accelerated by heating.

The simplified reaction sequence is as follows:

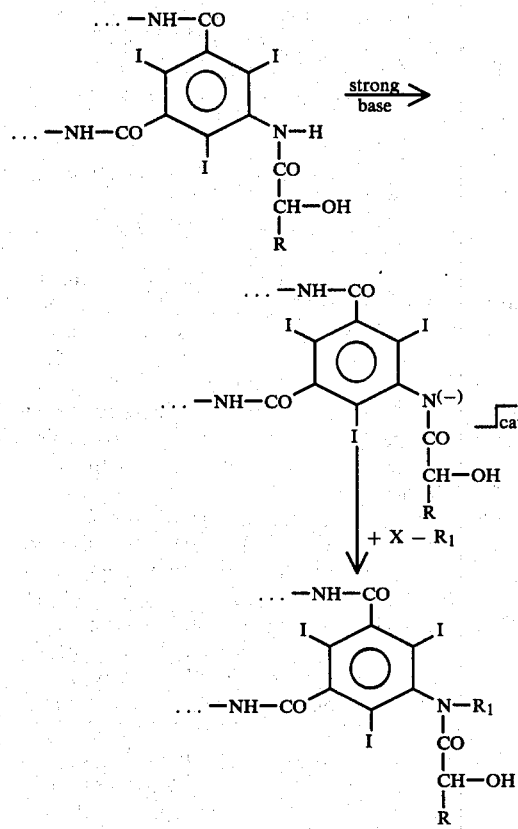

However, it is also possible to prepare a reactive derivative of a 5-(N-alkyl-α-hydroxyacyl-amino)-2,4,6-triiodo-isophthalic-acid of the general formula (V) and react this with dihydroxypropylamine or a functional derivative thereof and to hydrolytically split off the masking groups in the product obtained and liberate all of the hydroxy functions.

Acid derivatives suitable for use in this reaction are acid halides, and particularly acid chlorides, that is a 5-(N-alkyl-α-acyloxyacyl-amino)-2,4,6-triiodo-isophthalic acid dichloride or an appropriate acid anhydride with an organic or inorganic acid. Suitable organic acids include lower fatty acids, such as, for example, propionic acid, butyric acid, valeric acid or semi-esters of carbonic acid, such as, for example, monomethyl carbonate, monoethyl carbonate or monobenzyl carbonate. Suitable inorganic acids include hydrazoic acid, the semi-ester of sulfuric acid, phosphoric acid, phosphorous acid, dialkyl phosphate, e.g. diethyl phosphate.

The reaction with a dihydroxypropylamine is usually carried out in a solvent which is inert in this reaction, for example, in an aprotic solvent, such as, DMF, DMAC, etc., within a temperature range of about −10° C. to about +150° C.

In the reaction, the following compounds are preferably used as hydroxyalkylamines or their derivatives: 1,3-dihydroxyisopropylamine (serinol), 2,3-dihydroxypropylamine, tris-(hydroxymethyl)-aminomethane (2-amino-2-hydroxymethyl-1,3-propanediol), as well as ketals or acetals thereof, for example, 5-amino-2,2-dimethyl-1,3-dioxane, 4-aminomethyl-2,2-dimethyl-1,3-dioxolane, 5-amino-2-methyl-1,3-dioxane, 5-amino-2-phenyl-1,3-dioxane or 5-amino-1,3-dioxane.

For the introduction of the hydroxyacyl residues and for some reactions of compounds containing these, it is necessary to mask the hydroxy function. For this purpose, it is customary to use an acyloxy function A, consisting of a lower acyloxy residue, preferably, the acetyloxy residue, which can easily be converted in the final step into the hydroxy function by alkaline saponification.

It is also possible to start from the corresponding, easily accessible halogen acetyl compounds of formula (V), in which R=H and A=halogen, preferably chlorine, particularly for the synthesis of the hydroxyacetyl derivatives. The halogen acetyl group is easily converted by alkaline saponification into the terminal, desired, hydroxyacetyl group.

EXAMPLE 1

L-5-(N-methyl-α-hydroxypropionyl-amino)-2,4,6-triiodoisophthalic-acid-bis-(1,3-dihydroxyisopropylamide)

L-5-α-hydroxypropionyl-amino-2,4,6-triiodo-isophthalic-acid-bis-(1,3-dihydroxyisopropylamide) (58.3 g, 0.075 moles) is dissolved in 200 ml water and mixed with exactly the stoichiometric amount (0.075 moles) of 2 N NaOH. The solution has a pH of 11.9. It is evaporated to dryness under vacuum. The residue consists of the 5-N-sodium compound (Na salt) of L-5-α-hydroxypropionyl-amino-2,4,6-triiodo-isophthalic-acid bis-(1,3)-dihydroxyisopropylamide) and is dried under vacuum at 100° C. Equivalent weight of $C_{17}H_{21}I_3N_3NaO_8$ calc. 799.27; found 799.08.

The sodium salt so obtained (60 g=0.0075 moles) is dissolved in 200 ml of dimethylacetamide (DMAC) and, at 30° C., mixed dropwise with 12.7 g of methyl iodide (0.09 moles). The mixture is stirred for about 1 hour at 40° C. until the reaction has been completed according to chromatographic analysis. The reaction solution is evaporated under vacuum. The sirupy residue is stirred into 600 ml of acetone, the product (and NaI) precipitating. The precipitate is filtered off, dissolved in 400 ml of water and desalinated completely by percolating it first, through a cationic exchange resin (e.g. Amberlite ® IR 120) and, subsequently, through an anionic exchange resin (e.g. Amberlite ® IR 45) column. The column eluate is evaporated to complete dryness.

Yield: 42.2 g of L-5-(N-methyl-α-hydroxypropionyl-amino)-2,4,6-triiodo-isophthalic-acid-bis-(1,3-dihydroxyisopropylamide), that is, 71% of the theoretical yield.

Melting point (after recrystallization from abs. ethanol) ca. 250° C. (sinters at 190° C.);

Thin-layer chromatography (TLC) on silica gel: solvent chloroform/methanol/ammonia (25%)=6:3:1. $R_f$=0.29 and 0.33;

$C_{18}H_{24}I_3N_3O_8$: I calc. 48.12%, found 47.99%.

Water solubility: ≧100% (w/v) at 25° C.

The same compound is also obtained if the methyl iodide in the above-described starting material is replaced by 11.4 g of dimethyl sulfate (0.09 moles), the procedure being otherwise unchanged.

The d,L-5-(N-methyl-α-hydroxypropionyl-amino)-2,4,6-triiodo-isophthalic-acid-bis-(1,3-dihydroxyisopropylamide is obtained completely analogously by methylation of d,L-5-α-hydroxypropionylamino-2,4,6-triiodo-isophthalic-acid-bis-(1,3-dihydroxyisopropylamide), which has only limited solubility in water.

Melting point: 298°–300° C. (with decomposition)
TLC: $R_f$=0.34 and 0.39 with $CHCl_3/MeOH/NH_4OH$=6:3:1.
This product dissolves in water very readily. The solutions, however, are supersaturated.

EXAMPLE 2

L-5-(N-ethyl-α-hydroxypropionyl-amino)-2,4,6-triiodo-isophthalic-acid-bis-(1,3-dihydroxyisopropylamide The 5-N-sodium compound of L-5-α-hydroxypropionyl-amino-2,4,6-triiodo-isophthalic-acid-bis-(1,3 dihydroxyisopropylamide) (90 g, 0.112 moles), in 240 ml of DMAC, is reacted with 26.5 g of ethyl iodide (0.17 moles) and worked up as in Example 1. A total of 66 g of the title compound is obtained, that is, 73% of the theoretical yield.

Melting point: 295°–297° C. (with decomposition),
TLC: $R_f$=0.27. Solvent $CHCl_3/MeOH/NH_4OH$ (25%)=6:3:1.
$C_{19}H_{26}I_3N_3O_8$: I calc.=47.28%, I found=47.21%.
$[α]_D^{20}$=+18.83° (c=10% in water).

EXAMPLE 3

L-5-(N-propyl-α-hydroxypropionyl-amino)2,4,6-triiodo-isophthalic-acid-bis-(1,3-dihydroxyisopropylamide The 5-N-sodium compound of L-5-α-hydroxypropionylamino-2,4,6-triiodo-isophthalic-acid-bis-(1,3-dihydroxyisopropylamide) (38 g, 0.045 moles) in 120 of DMAC, is reacted with 7.5 g of propyl bromide (0.06 moles) at 80° C. as in Example 1. The product can be desalinated by partitioning it between butanol and water.

Yield: 18.43 g of L-5-(N-propyl-α-hydroxypropionyl-amino)-2,4,6-triiodo-isophthalic-acid-bis-(1,3-dihydroxyisopropylamide), that is, 50% of the theoretical yield.

Melting point: 149° C. (sinters at 142° C).
TLC: $R_f$=0.35; 0.42 and 0.48. Solvent: $CH_2Cl_2/CHCl_3$=10:3.
$C_{20}H_{28}I_3N_3O_8$: for iodine-calc. 46.47%; found 46.25%.
Water solubility: ≧100% (w/v) at 25° C.

EXAMPLE 4

L-5-(N-butyl-α-hydroxypropionyl-amino)-2,4,6-triiodo-isophthalic-acid-bis-(1,3-dihydroxyisopropylamide)

The sodium salt (80 g) of L-5-α-hydroxypropionylamino-2,4,6-triiodo-isophthalic-acid-bis-(1,3-dihydroxyisopropylamide)=IOPAMIDOL, in 240 ml of DMAC, is reacted at 40°–80° C. with 17.8 g of butyl bromide (0.13 moles). The product can be desalinated by partitioning it between methyl ethyl ketone and water (countercurrent extraction).

Yield: 30 g of L-5-(N-butyl-α-hydroxypropionyl-amino)-2,4,6-triiodo-isophthalic-acid-bis-(1,3-dihydroxy-isopropylamide).

Melting point (after reprecipitation from isopropanol/diisopropyl ether and repeated precipitation from water): 140°–145° C.

TLC: $R_f$=0.36; 0.46 and 0.51. Solvent $CH_2Cl_2/MeOH$=10:3.
$C_{21}H_{30}I_3N_3O_8$: for iodine-calc. 45.69%; found 45.88%.

Water solubility: ≧100% (w/v).

EXAMPLE 5

5-(N-methyl-hydroxyacetyl-amino)-2,4,6-triiodo-isophthalic-acid-bis-(1,3-dihydroxyisopropylamide)

The sodium salt (50 g) of 5-hydroxyacetylamino-2,4,6-triiodo-isophthalic-acid-bis-(1,3-dihydroxyisopropylamide) (0.064 moles), in 250 ml of DMAC, is reacted with 13.8 g of methyl iodide as in Example 1.

5-(N-methyl-hydroxyacetyl-amino)-2,4,6-triiodo-isophthalic-acid-bis-(1,3-dihydroxyisopropylamide) is obtained in a yield of 37.9 g, corresponding to 77% of the theoretical yield.

Melting point: 215°–220° C.,
TLC: $R_f$=0.45, Solvent: ethyl acetate/glacial acetic acid/water=15:3:5;
$C_{17}H_{22}I_3N_3O_8$: for iodine-calc. 48.99%; found 48.61%.

The 5-hydroxyacetylamino-2,4,6-triiodo-isophthalic-acid-bis-(1,3-dihydroxyisopropylamide), which is used as an intermediate, is obtained as follows according to the method described in German Pat. No. 2,547,789:

(A) 5-amino-2,4,6-triiodo-isophthalic acid dichloride (59.6 g) is reacted in DMAC with 34 g of acetoxyacetyl chloride (0.25 moles), 67.5 g of 5-acetoxyacetylamino-2,4,6-triiodo-isophthalic acid dichloride melting at 234°–235° C. being obtained.

(B) 5-acetoxyacetylamino-2,4,6-triiodo-isophthalic acid dichloride (150 g) in 810 ml of DMAC is treated with 80 g of tributylamine and then with 49.2 g of serinol (=1,3-dihydroxyisopropylamine) in 540 ml of DMAC. 5-acetoxyacetylamino-2,4,6-triiodo-isophthalic-acid-bis-(1,3-dihydroxyisopropylamide) (172 g) is obtained, which melts at about 190°–192° C. with decomposition. This compound is suspended in water and treated carefully at 45° C. with 1 N NaOH at a pH of 11, until the acetoxy group is completely hydrolyzed.

The solution obtained is desalinated by percolating it through a column of cationic exchange resin (Amberlite ® IR 120) and then through a column of anionic exchange resin (Amberlite ® IR 45). The eluate is evaporated to dryness and taken up in 90% ethanol, whereby the desired intermediate 5-hydroxyacetylamino-2,4,6-triiodo-isophthalic-acid-bis-(1,3-dihydroxyisopropylamide) is obtained as a crystalline product (73 g).

Melting point: 300° C. with decomposition.

EXAMPLE 6

5-(N-ethyl-hydroxyacetyl-amino)-2,4,6-triiodo-isophthalic-acid-bis-(1,3-dihydroxyisopropylamide)

Obtained by the reaction of 50 g of the sodium salt of 5-hydroxyacetylamino-2,4,6-triiodo-isophthalic-acid-bis-(1,3)-dihydroxyisopropylamide) with ethyl iodide.

Melting point: 210° C.,
$C_{18}H_{24}I_3N_3O_8$: for iodine: calc. 48.12%, found 48.10%.

EXAMPLE 7

L-5-(N-methyl-α-hydroxypropionyl-amino)-2,4,6-triiodo-isophthalic-acid-bis-(1,3-dihydroxyisopropylamide) Alternative Synthesis A solution of 14.5 g of L-5-(N-methyl-α-acetoxypropionylamino)-2,4,6-triiodo-isophthalic acid dichloride (0.02 moles) in 35 ml of DMF is stirred and treated dropwise at 0°–2° C. with 9.1 g of serinol (=1,3-dihydroxyisopropylamine) (0.1 moles) in 30 ml of DMF. Stirring is continued for an additional 3 hours at 20° C. and the reaction solution is subsequently evaporated to a syrup. The crude product is taken up in 100 ml of water, freed from adhering solvent by evacuation and, at 40°–50° C., brought to a pH of 11.6 with aqueous 2 N sodium hydroxide solution. The pH is kept at a constant value by the continuous addition of NaOH. In all, 29 ml of 2 N NaOH are consumed.

The alkaline solution obtained is diluted with 200 ml of water and desalinated by percolating it through a column of cationic exchange resin (Amberlite ® IR-120) and a column of anionic exchange resin (Amberlite ® IR-45). The column eluate is evaporated to dryness.

Yield: 11.08 g of L-5-(N-methyl-α-hydroxypropionyl-amino)-2,4,6-triiodo-isophthalic-acid-bis-(1,3-dihydroxyisopropylamide), that is, 70% of the theoretical yield.

Melting point (after repeated recrystallization from abs. ethanol)>280° C. (sinters at 210° C.)

TLC on silica gel: solvent ethyl acetate/glacial acetic acid/water=10:5:3. One spot at $R_f$ 0.29.

The L-5-(N-methyl-α-acetoxy-propionyl-amino)-2,4,6-triiodo-isophthalic acid dichloride, which is used as an intermediate, is obtained as follows:

(A) 5-amino-2,4,6-triiodo-isophthalic acid is treated in sulfuric acid with formaldehyde according to the method described in German Offenlegungsschrift 2,050,217, 5-methylamino-2,4,6-isophthalic acid, melting at 198°–200° C., being obtained.

TLC on silica gel with ethyl methyl ketone/ethanol/water/glacial acetic acid=20:8:5:1.5. $R_f$=0.55.

(B) 5-methylamino-2,4,6-triiodo-isophthalic acid (23 g) in 120 ml of thionyl chloride is boiled for 7 hours under reflux in the presence of 0.1 ml of quinoline. After completely distilling off the thionyl chloride, the residue is stirred into 120 g of ice water, which contains sodium chloride (125 g) and NaHCO$_3$ (12 g).

The product is extracted with ethyl acetate (200 ml). From the extract, 5-methylamino-2,4,6-triiodo-isophthalic acid dichloride is obtained by evaporation.

Melting point 167° C. TLC on silica gel with benzene/hexane=1:1; $R_f$=0.50.

$C_9H_4Cl_2I_3NO_2$ Cl calc. 11.62%, Cl found 11.74%, I calc. 62.44%, I found 62.74%.

(C) 5-methylamino-2,4,6-triiodo-isophthalic acid dichloride (12 g, 0.02 moles) in 30 ml of DMAC is reacted with 1-α-acetoxy-propionic acid dichloride (0.03 moles) added dropwise at 0°–2° C. Subsequently, stirring is continued for 1 to 2 hours at 20° C.

The reaction solution is stirred into ice water. The precipitated product is filtered off, dried and recrystallized from a little benzene.

L-5-(N-methyl-α-acetoxypropionylamino)-2,4,6-triiodo-isophthalic acid dichloride (14 g), melting at 187° C. –190° C., is obtained.

TLC on silica gel with hexane/chloroform/ethyl acetate=3:1:1, 2 spots with $R_f$ of 0.22 and 0.5.

$C_{14}H_{10}Cl_2I_3NO_5$: Cl calc. 9.79%; Cl found 9.80%, I calc. 52.59%; I found 52.46%.

EXAMPLE 8

L-5-(N-methyl-α-hydroxypropionyl-amino)-2,4,6-triiodo-isophthalic-acid-bis-(2,3-dihydroxypropylamide)

L-5-(N-methyl-α-acetoxypropionyl-amino)-2,4,6-triiodo-isophthalic acid dichloride (14.5 g, 0.02 moles) in 30 ml of DMF is treated by the dropwise addition of 9.4 g of 2,4-dihydroxypropylamine (=1-amino-2,3-propanediol) dissolved in 50 ml of DMF and reacted and worked up according to the method described in Example 7.

Yield: 10.8 g of L-5-(N-methyl-α-hydroxyproponyl-amino)-2,4,6-triiodo-isophthalic-acid-bis-(2,3-dihydroxypropylamide), corresponding to 68% of the theoretical yield.

Melting point (after recrystallization from ethanol): 195° C. (sinters at 187° C.).

TLC on silica gel: solvent-ethyl acetate/glacial acetic acid/water=10:5:3. One spot at $R_f$ 0.45.

$C_{18}H_{24}I_3N_3O_8.H_2O$: I calc. 47.05%, found 47.00%, $H_2O$ calc. 2.23%, found 2.8%.

EXAMPLE 9

5-(N-methyl-hydroxyacetyl-amino)-2,4,6-triiodo-isophthalic-acid-bis-(2,3-dihydroxypropylamide)

The 5-N sodium compound of 5-hydroxyacetylamino-2,4,6-triiodo-isophthalic-acid-bis-(2,3-dihydroxypropylamide) (49 g, 0.0625 moles), prepared as described in Example 1, is dissolved in 250 ml of DMAC and treated at 5° C. by the dropwise addition 13.5 g of methyl iodide. It is subsequently stirred for some hours.

The reaction solution is concentrated under vacuum, and the residue of the evaporation is treated with 300 ml methylene chloride, whereupon the product formed is precipitated in admixture with sodium iodide. The crude product is dissolved in water and desalinated with ion-exchange resin.

Yield: 36 g of 5-(N-methylhydroxyacetyl-amino)-2,4,6-triiodo-isophthalic-acid-bis-(2,3-dihydroxypropylamide), corresponding of 75% of the theoretical yield.

Melting point: 190°–191° C. (amorphous product).

TLC on silica gel: solvent-2 butanone/glacial acetic acid/water=15:3:5.

Spots at $R_f$ 0.48 and 0.40.

Solubility: very readily soluble in water and methanol. Solubility in ethanol limited. (in 20 parts by volume at the boiling point and in 35 parts by volume at 25° C.).

The 5-hydroxyacetylamino-2,4,6-triiodo-isophthalic-acid-bis-(2,3-dihydroxypropylamide), used as an intermediate, is obtained according to the method described in German Pat. No. 2,457,789 as follows:

To a solution of 24.4 g of 5-acetoxyacetylamino-2,4,6-triiodo-isophthalic acid dichloride (0.035 moles) in 60 ml of DMAC, there is added dropwise with stirring a solution of 15.9 g of 2,3-dihydroxypropylamine (=1-amino-2,3-dihydroxypropane) (0.175 moles) in 100 ml of DMAC.

An oily 5-acetoxyacetylamino-2,4,6-triiodo-isophthalic acid-bis-(2,3-dihydroxypropylamide) is obtained. This compound is taken up in 250 ml of water and treated carefully at 40° C. with 40 ml of 1 N sodium hydroxide until the acetoxy group is hydrolyzed off completely.

The solution obtained is desalinated by percolation through a column of cationic exchange resin (Amberlite ® IR-120) and a column of anionic exchange resin (Amberlite ® IR-45). The eluate is evaporated. After some time, crystallization takes place. By recrystallization from a little water, the desired intermediate, 5-hydroxyacetylamino-2,4,6-triiodo-isophthalic-acid-bis-(2,3-dihydroxypropylamide) is obtained in a pure form.

Melting point: 290° C.

TLC: $R_f=0.24$, solvent: ethyl acetate/ethanol/ammonia (25%)=15:7:6.

$C_{16}H_{20}I_3N_3O_8$: C calc. 25.18%, found 25.01%, I calc. 49.89%, found 49.75%. EXAMPLE 10

5-(N-methyl-hydroxyacetyl-amino)-2,4,6-triiodo-isophthalic-acid-bis-(2,3-dihydroxypropylamide)

(A) 5-hydroxyacetylamino-2,4,6-triiodo-isophthalic-acid-bis-(2,3-dihydroxypropylamide) (90 g, 0.117 moles) is suspended in 700 ml of DMAC and treated at 40° C. with 95 g of a solution of sodium hydroxide in methanol (1.233 moles). The 5-N sodium compound is formed. Methanol, water of reaction and a portion of the DMAC are distilled off under vacuum. A 496 g solution containing 0.234 moles of the 5-N-Na compound of 5-hydroxyacetylamino-2,4,6-triiodo-isophthalic-acid-bis-(2,3-dihydroxypropylamide) is obtained.

(B) The solution (390 g, 0.091 moles), described in Section A, is added dropwise with stirring and within 45 minutes to a solution of 13 g of methyl bromide (0.137 moles) in 160 g of DMAC at 0° C. Stirring is then continued at 0° to 5° C. for some hours.

Yield: 60.1 g of 5-(N-methyl-hydroxyacetyl-amino)-2,4,6-triiodo-isophthalic-acid-bis-(2,3-dihydroxypropylamide), that is, 85% of the theoretical yield.

TLC on silica gel with a solvent consisting of acetyl acetate/glacial acetic acid/water=10:5:3. Spots at $R_f$ 0.3 and 0.45. The product can be recrystallized from 95% ethanol.

Melting point: 305°–310° C. with decomposition. The melting point is not very characteristic.

(C) A solution (390 g, 0.091 moles) of the sodium compound of 5-hydroxyacetylamino-2,4,6-triiodo-isophthalic-acid-bis-(2,3-dihydroxypropylamide), described in Section A, is added dropwise with stirring and within 50 minutes to a solution of 13.8 g of dimethyl sulfate (0.109 moles) in 150 ml of DMAC. The reaction solution is stirred for some hours and subsequently worked up according to the method described in Example 1.

Yield: 62.4 g of 5-(N-methyl-hydroxyacetyl-amino)-2,4,6-triiodo-isophthalic-acid-bis-(2,3-dihydroxypropylamide), that is, 88% of the theoretical yield.

Melting point (after recrystallization from 95% ethanol): 305°–310° C. with decomposition.

EXAMPLE 11

5-(N-methyl-hydroxyacetyl-amino)-2,4,6-triiodo-isophthalic-acid-bis-( 2,3-dihydroxypropylamide) Alternative Synthesis A solution of 28.4 g of 5-(N-methyl-acetoxyacetylamino)-2,4,6-triiodo-isophthalic acid dichloride in 90 ml of DMAC is added dropwise, with stirring and within 45 minutes to a solution of 18.2 g of 1-amino-2,3-propanediol in 70 ml of DMAC at 5° C. The reaction mixture is stirred for some hours and subsequently evaporated under vacuum to a syrup. The residue is triturated with methylene chloride and acetone and the solvet decanted off. The residue is freed under vacuum from adhering solvent, taken up in 200 ml of water and carefully kept at a pH of 11 to 11.5 at 45° C. by the addition of a total of 50 ml of 2 N sodium hydroxide solution, during which process the acetoxy group is hydrolyzed off.

The solution obtained is desalinated by percolating it first through a column of cationic exchange resin (e.g. 200 ml of Amberlite ® IR-120) and then through a a column of an anionic exchange resin (e.g. 250 ml of Amberlite ® IR-45). The eluate is evaporated, the residue dissolved in methanol and the solution treated with methylene chloride, whereby the desired product is precipitated.

Yield: 22 g of the title compound, that is, 71% of the theoretical yield.

Melting point: ca. 190° C. (sinters at ca. 165° C.).

TLC on silica gel: solvent consisting of 2-butanol/glacial acetic acid/water=15:3:5. Spots at $R_f$ 0.48 and 0.40.

$C_{17}H_{22}I_3N_3O_8$: I calc. 48.99%, found 48.69%.

The compound is very soluble in water (3 g in 1 ml of water) and in methanol (100 w/v).

The 5-(N-methyl-acetoxy-acetyl-amino)-2,4,6-triiodo-isophthalic acid dichloride, which is used as an intermediate, is obtained as follows:

A solution of 32 g of 5-methylamino-2,4,6-triiodoisophthalic acid dichloride (0.0525 moles in 80 ml of DMAC is treated dropwise at 0° to 5° C. with stirring with 10.7 g of acetoxyacetylchloride. Subsequently, stirring is continued over night and at room temperature. The reaction solution is stirred into ice water. A total of 36.7 g of 5-(N-methylacetoxyacetylamino)-2,4,6-triiodo-isophthalic acid dichloride, melting at 198°–200° C., are obtained, corresponding to a theoretical yield of 98.8%.

TLC on silica gel with benzene/methanol=10:3, $R_f=0.64$.

$C_{13}H_8Cl_2I_3NO_5$ calc. Cl 9.9%, I 53.3% found Cl 10.05% I 53.41%.

EXAMPLE 12

5-(N-methyl-hydroxyacetyl-amino)-2,4,6-triiodo-isophthalic-acid-bis-(R(+)2,3-dihydroxypropylamide)

This compound is obtained similarly as the corresponding racemic compound by, as described in Example 11, adding a solution of 20.2 g of 5-(N-methylacetoxyacetyl-amino)-2,4,6-triiodo-isophthalic acid dichloride in 40 ml of DMAC dropwise to a solution of 7 g of R(+)1-amino-2,3-propanediol (0.077 moles) in 40 ml of DMAC, in which 10.8 g of potassium carbonate (0.077 moles) are suspended. The reaction mixture is stirred for some hours and subsequently worked up as described in Example 10.

A total of 15.2 g of the title compound, corresponding to a theoretical yield of 69.5%, are obtained.

Melting point: 283°–284° C.

TLC: $R_f=0.24$. Solvent-isopropanol/isobutanol/ammonia (25%)=7:7:6.

$C_{17}H_{22}I_3N_3O_8$: I calc. 48.99%, found 48.74%.

$[\alpha]_D^{20}=+4.85°$, $[\alpha]_{436}^{20}=+11.1°$ (c=10% in water).

EXAMPLE 13

5-(N-methyl-hydroxyacetyl-amino)-2,4,6-triiodo-isophthalic-acid-bis-(2,3-dihydroxypropylamide)

(A) 5-(N-methyl-hydroxyacetyl-amino)-2,4,6-triiodo-isophthalic-acid-bis-(2,3-isopropylidenedihydroxypropylamide)=5-(N-methylhydroxyacetyl-amino)-2,4,6-triiodo-isophthalic-acid-bis-(2,3-dimethyl-1,3-dioxolan-(4)-ylmethylamide).

A solution of 17.8 g of 5-(N-methyl-acetoxyacetylamino-2,4,6-triiodo-isophthalic acid dichloride (0.025 moles) in 50 ml of DMAC is treated dropwise with stirring at 5°–8° C. with a solution of 16 g of 4-aminomethyl-2,2-dimethyl-1,3-dioxolan (0.122 moles).

Stirring is continued for 18 hours at room temperature. The precipitated hydrochloride is filtered off and the filtrate is evaporated to dryness under vacuum. The residue from the evaporation is suspended in water, filtered, dissolved in aqueous methanol and treated at 50°–55° C. with 2 N sodium hydroxide at a pH of 10.5 to 11, whereby the acetoxy group is hydrolyzed off completely. The solution obtained is neutralized exactly by the careful addition of hydrochloric acid, filtered until clear and evaporated to dryness. The residue is taken up in water from which the 5-(N-methyl-hydroxy-acetyl-amino)-2,4,6-triiodo-isophthalic-acid-bis-(2,3-isopropylidenedihydroxypropylamide) crystallizes out.

Yield: 15.2 g, corresponding to 71% of the theoretical yield.

Melting point: (after recrystallization from dilute methanol) 180°–181° C.

TLC: $R_f = 0.295$, solvent—chloroform/hexane/methanol = 3:3:1.

$C_{23}H_{30}I_3N_3O_8$: I calc. 44.41%, found 44.08%.

This compound is very soluble in methanol, ethanol and chloroform and, on the other hand, only slightly soluble in water.

B. 5-(N-methyl-hydroxyacetyl-amino)-2,4,6-triiodo-isophthalic-acid-bis-(2,3-dihydroxypropylamide).

A solution of 15 g of 5-(N-methyl-hydroxyacetyl-amino)-2,4,6-triiodo-isophthalic-acid-bis-(2,3-isopropylidenedihydroxypropylamide) in 185 ml of 0.1 N aqueous hydrochloric acid and 185 ml of methanol is kept for 5 hours at 50° C. with stirring. The reaction solution is freed from hydrochloric acid by percolation through a column filled with 75 ml of a weakly basic ion-exchange resin, e.g., Amberlite ® IR-45, and evaporated to dryness.

Yield: 12.2 g of 5-(N-methyl-hydroxyacetyl-amino)-2,4,6-triiodo-isophthalic-acid-bis-(2,3-dihydroxypropylamide) that is, 90% of the theoretical yield.

Melting point: 190° C. (amorphous product).

After crystallization from 95% ethanol Melting point: 300° C. with decomposition.

Use:

Of the compounds described in the above Examples, the 5-(N-methyl-α-hydroxy-acyl-amino)-2,4,6-triiodo-isophthalic-acid-bis-(hydroxyalkylamides) of formula (II) are in general preferred because they are more water-soluble as well as more readily accessible than the higher N-alkyl derivatives thereof.

Within the preferred amounts of formula (II), the hydroxyacetyl derivatives are usually preferred to the α-hydroxypropionyl derivatives, because they are more easily synthesized, have no center of asymmetry and nevertheless generally have the required high water-solubility.

Because they are easily synthesized, the 2,3-dihydroxypropylamides are the preferred hydroxyalkylamides. A typical representative of this group is the 5-(N-methyl-hydroxyacetylamino)-2,4,6-triiodo-isophthalic-acid-bis-(2,3-dihydroxypropylamide) (Compound A). This compound is distinguished by its comparatively particularly high water-solubility, by the low viscosity of its aqueous solutions and by the high stability.

In the following table, important properties of Compound A are compared with those of two previously known nonionic X-ray contrasting materials, namely, with B: L-5-α-hydroxypropionylamino-2,4,6-triiodo-isophthalic-acid-bis-(1,3-dihydroxyisopropylamide) (international non-proprietary name = IOPAMIDOL);

C: 3-acetylamino-4-N-methyl-acetylamino-2,4,6-triiodobenzoylglucosamine (international non-proprietary name (I.N.N.) = METRIZAMIDE)

TABLE 1

| Compound | Solubility in Water in % (w/v) at 20° C. | °C. | Viscosity in Centipoise (cP) Aqueous solutions containing | |
|---|---|---|---|---|
| | | | 300 mg I/ml | 400 mg I/ml |
| A | >100 | 20° C. | 7.55 | 22.0 |
| | | 37° C. | 4.19 | 9.87 |
| B | 89 | 20° C. | 8.95 | 40.6 |
| | | 37° C. | 4.70 | 16.1 |
| C | ~80 | 20° C. | 11.7 | 77.8 |
| | | 37° C. | 5.98 | 26.9 |

TABLE 2

| Compound | mg I/ml | Osmolality (mOsm/kg) 37° C. | Osmotic Pressure atm 37° C. |
|---|---|---|---|
| A | 250 | 452 | 11.52 |
| | 300 | 536 | 13.64 |
| | 350 | 628 15.98 | |
| B | 250 | 514 | 13.09 |
| | 300 | 619 | 15.76 |
| | 350 | 737 | 18.77 |

It is clearly evident from Table 1 that the inventively obtained Compound A has a higher water solubility and an appreciably lower viscosity than the previously known Compounds B and C. Solutions of A can therefore be used at a higher concentration and, because of their low viscosity, can nevertheless be injected without difficulties. It is evident from Table 2 that the osmotic pressure of the inventively obtained Compound A is less than that of IOPAMIDOL. The stress on the organism is therefore less when administering Compound A than when administering Compound B.

The novel 5-(N-alkyl-α-hydroxyacyl-amino)-2,4,6-triiodo-isophthalic-acid-bis-(hydroxyalkyl-amide) of the general formula (I) are used primarily in the form of their aqueous solutions.

Depending on the intended purpose, ca. 15 to 85% solutions w/v (100% = 100 g of contrasting material per 100 ml of solution) with a content of about 60 to about 420 mgI/ml are used. Concentrated solutions are preferred. The nature of their application depends on the organ which is to be made visible.

For vasography, the solutions are injected or infused into the appropriate blood vessels.

For urography, the solutions are injected or infused intravenously.

For the enhancement of contrast in computer tomography, the solutions are, depending on the organ or tissue contrast to be intensified, either introduced by intravenous administration into the blood stream or concentrated by selective injection in the vascular system of a particular organ or of a body cavity.

For myelography and radiculography, the solutions are installed after lumbar or suboccipital puncture. In the case of ventriculography, the ventricles are punctured directly.

| Dosage: | |
|---|---|
| Myelography | ca. 5–15 ml |
| Radiculography | ca. 3–5 ml |

| -continued | |
|---|---|
| Dosage: | |
| Ventriculography | ca. 1-2 ml |

Solutions of X-ray contrasting materials are easily prepared because it is unnecessary to prepare salt solutions.

For example, the pure 2,4,6-triiodo-isophthalic amides, obtained according to the preceding examples, are dissolved under sterile conditions in the required amount of doubly distilled water, filtered, filled into serum bottles or ampoules and subsequently sterilized. The triiodo-isophthalic acid amides of the present invention are not decomposed by heat sterilization.

EXAMPLE 14

Injection Solutions Containing 5-(N-methyl-hydroxyacetyl-amino)-2,4,6-triiodo-isophthalic-acid-bis-(2,3-dihydroxypropylamide) = Compound A

| Composition of 20 ml Aliquots of Solution | | Iodine Content of Injection Solution in mg/ml | | |
|---|---|---|---|---|
| | | 200 | 300 | 420 |
| Compound A | g | 8.16 | 12.25 | 17.15 |
| Di-sodium-calcium salt of ethylenediamine-tetra-acetic acid hexahydrate | mg | 5.2 | 7.8 | 11 |
| Tromethamine (tris-(hydroxymethyl)-aminomethane) | mg | 9.5 | 14.2 | 20 |
| Doubly distilled water to | ml | 20 | 20 | 20 |
| Density at 37° C. | d | 1.207 | 1.316 | 1.453 |
| Viscosity at 37° C. | cP | 1.87 | 4.19 | 20.03 |

(cP = Centipoise)

Procedure: The sodium-calcium salt of ethylenediaminetetra-acetic acid, the tromethamine and the contrasting material are dissolved in doubly distilled water. The pH of the solution is adjusted, if necessary, to ca. 7 by the addition of 1 N hydrochloric acid. The volume is made up to 20 ml. The solution is filtered using a membrane of 0.45 mµ. The filtrate is filled into ampoules and sterilized for 30 minutes at 120° C.

EXAMPLE 15

| Injection Solution | |
|---|---|
| 5-(N—methyl-hydroxyacetyl-amino)-2,4,6-triiodo-isophthalic-acid-bis-(1,3-dihydroxyisopropylamide) | 82 g |
| 5-(N—methyl-hydroxyacetyl-amino)-2,4,6-triiodo-isophthalic-acid-bis-(2,3-dihydroxypropylamide) | 20.5 g |
| Sodium carbonate | 0.4 g |
| Disodium salt of ethylenediamine-tetraacetic acid | 0.02 g |
| Doubly distilled water to a volume of | 125 ml |

Procedure: The combined components are diluted to 125 ml with doubly distilled water, filtered, filled under hygienically satisfactory conditions into ampoules under nitrogen and subsequently sterilized. Iodine content: 400 mg/ml.

EXAMPLE 16

| Infusion Solution | |
|---|---|
| 5-(N—methyl-α-hydroxypropionylamino)-2,4,6-triiodo-isophthalic-acid-bis-(1,3-dihydroxypropylamide) | 155.9 g |
| Disodium salt of ethylenediaminetetra-acetic acid | 0.02 g |
| Doubly distilled water up to a volume of | 250 ml |

Procedure: The combined components are diluted to 250 ml, filled under nitrogen into a infusion flask and sterilized.

Iodine content: 300 mg/ml.

What is claimed is:

1. 5-(N-alkyl-α-hydroxyacylamino)-2,4,6-triiodoisophthalic-acid-bis-(hydroxyalkylamides) having the formula (I)

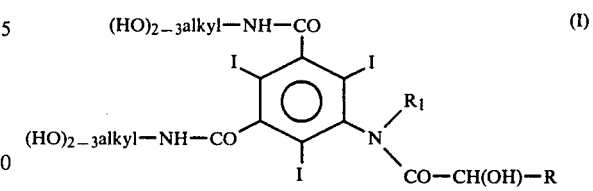

in which (OH)$_{2-3}$alkyl is 1,3-dihydroxyisopropyl, 2,3-dihydroxypropyl or 1,3-dihydroxy-2-hydroxy-methylisopropyl, R is hydrogen or methyl, and R$_1$ is an alkyl residue with 1 to 5 carbon atoms.

2. 5-(N-methyl-α-hydroxyacyl-amino)2,4,6-triiodo-isophthalic-acid-bis-(hydroxyalkylamides) having the formula (II)

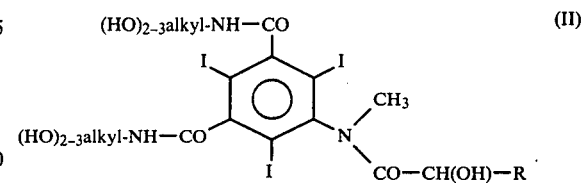

in which (HO)$_{2-3}$alkyl is 1,3-dihydroxyisopropyl, or 2,3-dihydroxypropyl or 1,3-dihydroxy-2-hydroxymethylisopropyl, and R is hydrogen or methyl.

3. 5-(N-methyl-hydroxyacetyl-amino)-2,4,6-triiodo-isophthalic-acid-bis-(2,3-dihydroxypropylamide).

4. 5-(N-methyl-α-hydroxypropionyl-amino)-2,4,6-triiodo-isophthalic-acid-bis-(1,3-dihydroxyisopropylamide).

5. In an X-ray contrasting composition containing a radio-opaque component and a pharmacologically acceptable carrier therefor, the improvement which comprises said radio-opaque component being

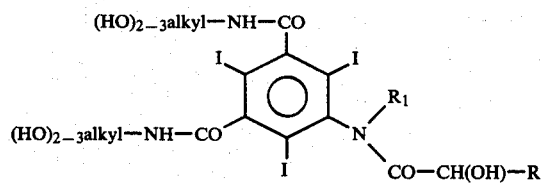

in which
(OH)$_{2-3}$alkyl is 1,3-dihydroxyisopropyl, 2,3-dihydroxypropyl, or 1,3-dihydroxy-2-hydroxy-methyl-isopropyl,
R is hydrogen or methyl, and
R$_1$ is an alkyl residue with 1 to 5 carbon atoms.

6. In a method for enhancement of the visualization of vessels in a patient wherein an X-ray contrasting composition is injected into the vessel, the improvement which comprises said X-ray contrasting composition comprising a radio-opaque effective amount of

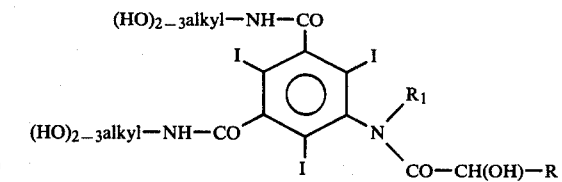

in which
(OH)$_{2-3}$alkyl is 1,3-dihydroxyisopropyl, 2,3-dihydroxypropyl, or 1,3-dihydroxy-2-hydroxy-methyl-iso-propyl,
R is hydrogen or methyl, and
R$_1$ is an alkyl residue with 1 to 5 carbon atoms,
and a carrier.

* * * * *